(12) United States Patent
Suzuki et al.

(10) Patent No.: US 10,648,854 B2
(45) Date of Patent: May 12, 2020

(54) RADIATION IMAGING APPARATUS HAVING HOUSING AND CORNER MEMBERS OF DIFFERENT MATERIALS AND RADIATION IMAGING SYSTEM

(71) Applicant: CANON KABUSHIKI KAISHA, Tokyo (JP)

(72) Inventors: Masataka Suzuki, Kawasaki (JP); Hidetomo Suwa, Machida (JP); Kensuke Kobayashi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/142,609

(22) Filed: Sep. 26, 2018

(65) Prior Publication Data

US 2019/0025116 A1  Jan. 24, 2019

Related U.S. Application Data

(63) Continuation of application No. 15/225,976, filed on Aug. 2, 2016, now Pat. No. 10,119,859.

(30) Foreign Application Priority Data

Aug. 7, 2015 (JP) .................................. 2015-157501

(51) Int. Cl.
*A61B 6/10* (2006.01)
*G01J 1/42* (2006.01)
*G03B 42/04* (2006.01)
*A61B 6/00* (2006.01)
*G01T 1/20* (2006.01)

(52) U.S. Cl.
CPC ............ *G01J 1/4228* (2013.01); *A61B 6/102* (2013.01); *A61B 6/4283* (2013.01); *G01T 1/2018* (2013.01); *G03B 42/04* (2013.01)

(58) Field of Classification Search
CPC ...... A61B 6/102; A61B 6/4283; G01J 1/4228; G01T 1/2018; G10H 1/348; G03B 42/04
USPC .............................................. 250/239, 208.1
See application file for complete search history.

(56) References Cited

U.S. PATENT DOCUMENTS

| 6,560,092 | B2 | 5/2003 | Itou et al. |
| 7,435,967 | B2 | 10/2008 | Ertel et al. |
| 7,488,946 | B2 | 2/2009 | Hennessy et al. |
| 7,569,831 | B2 | 8/2009 | Jadrich et al. |
| 7,582,877 | B2 | 9/2009 | Dobrusskin et al. |
| 7,947,960 | B2 | 5/2011 | Wu et al. |

(Continued)

FOREIGN PATENT DOCUMENTS

| CN | 101116033 | 1/2008 |
| CN | 101160012 | 4/2008 |

(Continued)

*Primary Examiner* — Que Tan Le
(74) *Attorney, Agent, or Firm* — Venable LLP (57) ABSTRACT

A radiation imaging apparatus includes a radiation detection panel, a housing configured to accommodate the radiation detection panel, and a buffer member. The housing has an opening in a corner. The buffer member includes a first portion fixed inside the housing and a second portion protruding from the opening of the housing to an outside of the housing. An elastic modulus of the second portion of the buffer member is lower than an elastic modulus of a portion of the housing which forms the opening.

20 Claims, 9 Drawing Sheets

(56) References Cited

U.S. PATENT DOCUMENTS

| | | | |
|---|---|---|---|
| 8,324,584 | B2 | 12/2012 | Sumi |
| 8,637,822 | B2 * | 1/2014 | Namekawa ............ G03B 42/04 250/336.1 |
| 8,744,044 | B2 | 6/2014 | Suwa et al. |
| 8,901,508 | B2 | 12/2014 | Lee et al. |
| 2005/0017188 | A1 | 1/2005 | Yagi |
| 2007/0138400 | A1 | 6/2007 | Ertel et al. |
| 2008/0078940 | A1 | 4/2008 | Castleberry et al. |
| 2013/0292577 | A1 | 11/2013 | Lee et al. |
| 2019/0025116 | A1 | 1/2019 | Suzuki et al. |

FOREIGN PATENT DOCUMENTS

| | | |
|---|---|---|
| CN | 101385648 | 3/2009 |
| CN | 101507610 | 8/2009 |
| JP | H09-005722 | 1/1997 |
| JP | 2001-337743 | 12/2001 |
| JP | 2003-042701 | 2/2003 |
| JP | 2008-090304 | 4/2008 |
| JP | 4248940 | 1/2009 |
| JP | 2010-156598 | 7/2010 |
| JP | 2011-058999 | 3/2011 |
| JP | 2012-125381 | 7/2012 |
| JP | 2013-257198 | 12/2013 |
| JP | 2014-066555 | 4/2014 |
| JP | 2017-036968 | 2/2017 |
| KR | 20-1999-0038919 | 11/1999 |
| KR | 10-2012-0053358 | 5/2012 |

* cited by examiner

RADIATION IMAGING APPARATUS HAVING HOUSING AND CORNER MEMBERS OF DIFFERENT MATERIALS AND RADIATION IMAGING SYSTEM

This application is a continuation of application Ser. No. 15/225,976 filed Aug. 2, 2016, which in turn claims the benefit of Japanese Patent Application No. 2015-157501, filed Aug. 7, 2015 which are hereby incorporated by reference herein in their entirety.

BACKGROUND OF THE INVENTION

Field of the Invention

The present invention relates to a radiation imaging apparatus and a radiation imaging system.

Description of the Related Art

A portable radiation imaging apparatus called an electronic cassette has been put into practice. When the portable radiation imaging apparatus is dropped, the resulting impact on the radiation imaging apparatus may break or deform the housing of the radiation imaging apparatus. Various countermeasures against such breakage or deformation have been proposed. Japanese Patent No. 4248940 proposes a technique of forming a housing by using an outer shell and an inner shell and filling the space between the outer shell and the inner shell with a shock absorber. Japanese Patent Laid-Open No. 2013-257198 proposes a technique of chamfering the corners of a housing and attaching detachable shock absorbers to the chamfered surfaces.

The outer surface of the housing disclosed in Japanese Patent No. 4248940 is formed from only an outer shell. When the outer shell is formed from a material having a high elastic modulus, it is possible to reduce the deformation of the overall housing when it is dropped. However, a stress concentrates on the outer shell. This may break the outer shell. In contrast to this, if the elastic modulus of the outer shell is decreased, it is difficult to reduce the deformation of the overall housing. In addition, as disclosed in Japanese Patent Laid-Open No. 2013-257198, when a shock absorber is attached to the outer surface of the housing, the dropping impact of the radiation imaging apparatus is transmitted to the housing through the shock absorber. This may distort or deform the overall housing. As described above, it is difficult for the existing methods to reduce both the breakage and deformation of the housing.

SUMMARY OF THE INVENTION

An aspect of the present invention provides a technique for reducing the deformation and breakage of the housing caused by impact on the radiation imaging apparatus.

According to some embodiments, a radiation imaging apparatus comprising: a radiation detection panel; a housing configured to accommodate the radiation detection panel; and a buffer member, wherein the housing has an opening in a corner, the buffer member includes a first portion fixed inside the housing and a second portion protruding from the opening of the housing to an outside of the housing, and an elastic modulus of the second portion of the buffer member is lower than an elastic modulus of a portion of the housing which forms the opening, is provided.

According to other embodiments, a radiation imaging apparatus comprising: a radiation detection panel; a housing configured to accommodate the radiation detection panel; and a buffer member, wherein the housing has an opening in a corner, the buffer member includes a first portion present inside the housing and a second portion protruding from the opening of the housing to an outside of the housing, an elastic modulus of the second portion of the buffer member is lower than an elastic modulus of a portion of the housing which forms the opening, and the first portion of the buffer member has a frame shape surrounding the radiation detection panel, is provided.

According to yet other embodiments, a radiation imaging apparatus comprising: a radiation detection panel; a housing configured to accommodate the radiation detection panel; and a buffer member, wherein the buffer member forms part of an outer shell of the radiation imaging apparatus and is arranged at a corner of the housing through another member different from the housing, is provided.

According to still other embodiments, a radiation imaging system comprising: one of radiation imaging apparatuses described above; and a signal processing unit for processing a signal obtained by the radiation imaging apparatus, is provided.

Further features of the present invention will become apparent from the following description of exemplary embodiments (with reference to the attached drawings).

DESCRIPTION OF THE EMBODIMENTS

The embodiments of the present invention will be described below with reference to the accompanying drawings. The same reference numerals denote the same elements throughout various embodiments, and a repetitive description of them will be omitted. In addition, the respective embodiments can be changed and combined as needed.

Figures 1A, 1B:
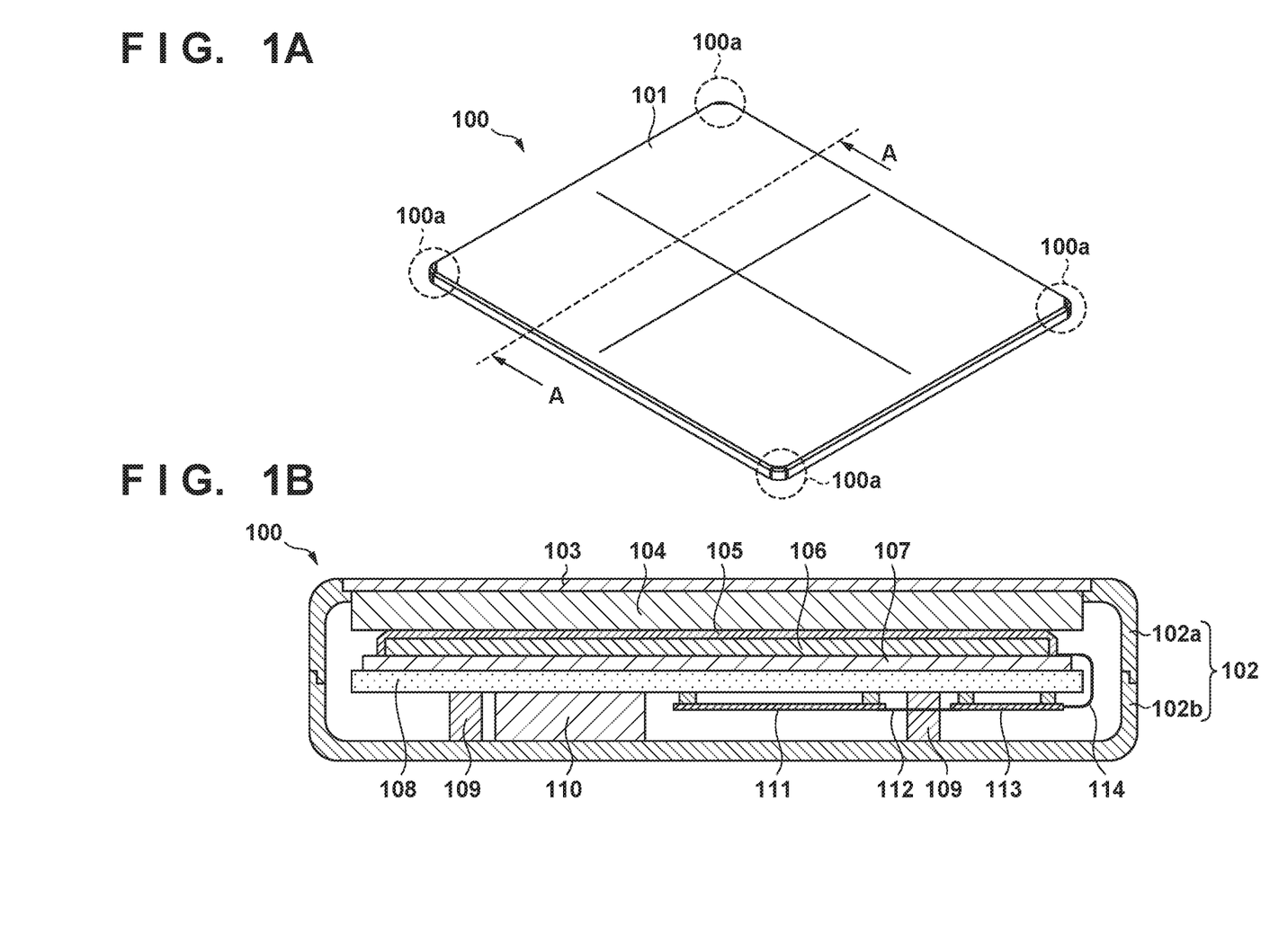
FIGS. 1A and 1B illustrate a radiation imaging apparatus according some embodiments of the present invention.

The arrangement of a radiation imaging apparatus 100 according to some embodiments of the present invention will be described with reference to FIGS. 1A and 1B. FIG. 1A is a perspective view of the radiation imaging apparatus 100. FIG. 1B is a sectional view taken along a line A-A in FIG. 1A. The radiation imaging apparatus 100 includes a housing 101 and constituent elements housed in the housing 101. In the following description, the surface (the surface on the upper side in FIG. 1B) of the radiation imaging apparatus 100 which is irradiated with radiation will be referred to as the incident plane. The surface (the surface on the lower side in FIG. 1B) on the opposite side to the incident plane will be referred to as the reverse surface, and surfaces connecting the incident plane and the reverse surface will be referred to as side surfaces. The incident plane, reverse surface, and side surfaces of the radiation imaging apparatus 100 respectively correspond to the incident plane, reverse surface, and side surfaces of the housing 101. A portion of the housing 101 which forms the incident plane will be referred to as an obverse side portion. Likewise, a portion of the housing 101 which forms the reverse surface will be referred to as a reverse side portion, and portions forming the side surfaces will be referred to as side walls. The side walls connect the obverse side portion to the reverse side portion. The radiation imaging apparatus 100 has four corners 100a. The corners 100a of the radiation imaging apparatus 100 correspond to the corners of the housing 101.

The housing 101 includes an upper cover member 102a, a lower cover member 102b, and a radiation transmitting plate 103. The upper cover member 102a and the lower cover member 102b constitute an outer shell 102 of the housing. The upper cover member 102a and the lower cover member 102b are in contact with each other at the side surfaces of the radiation imaging apparatus 100. The upper cover member 102a and the lower cover member 102b may be coupled to each other at the side surfaces of the radiation imaging apparatus 100 or may be coupled to each other through another portion. The upper cover member 102a has a frame shape, with the radiation transmitting plate 103 being fitted in an opening formed in the frame shape. The radiation transmitting plate 103 and part of the upper cover member 102a constitute the observe-side member of the housing 101. Part of the lower cover member 102b forms the reverse surface portion of the housing 101. Part of the upper cover member 102a and part of the lower cover member 102b constitute the side walls of the housing 101.

The radiation imaging apparatus 100 includes constituent elements to be described below, such as a sensor board 107 and a scintillator layer 106, inside the housing 101. The scintillator layer 106 is located between the sensor board 107 and the radiation transmitting plate 103. The scintillator layer 106 converts radiation entering the housing 101 through the radiation transmitting plate 103 into light. The sensor board 107 includes a sensor (for example, a photoelectric conversion element which converts light into charge) which converts light obtained by the scintillator layer 106 into an electrical signal and a switch element (for example, a TFT) for reading out the electrical signal to the outside of the sensor board 107. The sensor board 107 may include a plurality of pixels each constituted by a sensor and a switch element. The plurality of pixels may be arranged in a two-dimensional array pattern. The sensor board 107 and the scintillator layer 106 constitute a detection panel which detects radiation (that is, a radiation detection panel). The surface of the scintillator layer 106 is covered by a protective layer 105 having moisture resistance. The radiation imaging apparatus 100 exemplarily shown in FIGS. 1A and 1B has a so-called indirect type detection panel. Instead of this, however, the radiation imaging apparatus 100 may have a direct type detection panel which directly converts radiation into an electrical signal.

The sensor board 107 is connected to a circuit board 113 via a flexible cable 114. The circuit board 113 is connected to a circuit board 111 via a flexible cable 112. Circuits for reading out signals from the sensor board 107 and processing the readout signals and circuits for controlling the operation of the sensor board 107 are respectively arranged on the circuit boards 111 and 113. A battery 110 supplies power to the sensor board 107 and the circuit boards 111 and 113. The radiation imaging apparatus 100 may have a power supply circuit which externally supplies power to each constituent element, in place of the battery 110.

The detection panel (more specifically, the sensor board 107) is supported by a base 108. The base 108 is fixed or in contact with the lower cover member 102b through columnar supports 109. The circuit boards 111 and 113 and the battery 110 are arranged on the reverse surface side (on the opposite side to the detection panel) of the base 108. A buffer layer 104 formed from a foaming agent or the like is arranged between the detection panel (more specifically, the protective layer 105) and the radiation transmitting plate 103.

Figure 2A:
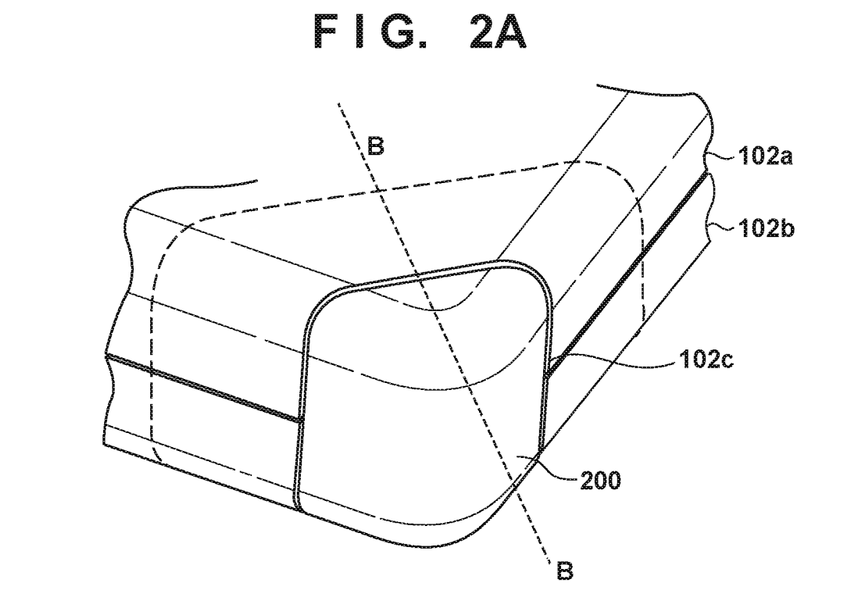
FIGS. 2A and 2B are views for explaining a buffer member according to some embodiments of the present invention.
Figure 2B:
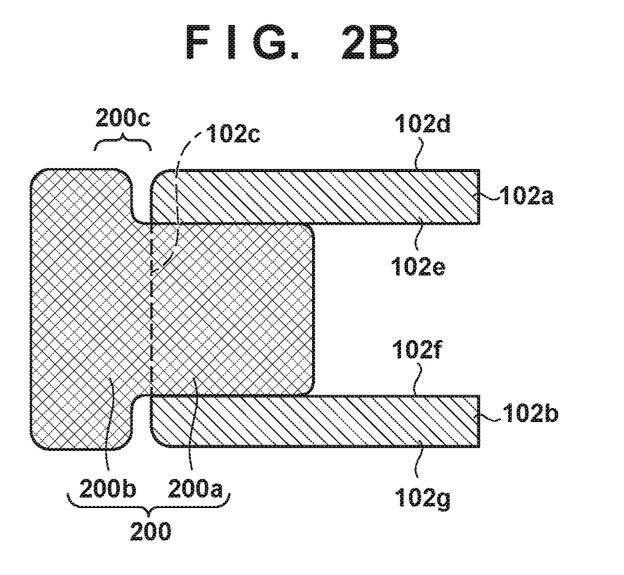

The structure of the corner 100a of the radiation imaging apparatus 100 will be described with reference to FIGS. 2A and 2B. FIG. 2A is a perspective view of the corner 100a of the radiation imaging apparatus 100. FIG. 2B is a sectional view taken along a line B-B in FIG. 2A. As shown in FIG. 2B, a surface of the upper cover member 102a which faces the outside of the housing 101 will be referred to as an outer surface 102d, and a surface of the upper cover member 102a which faces the inside of the housing 101 will be referred to as an inner surface 102e. A surface of the lower cover member 102b which faces the outside of the housing 101 will be referred to as an outer surface 102g, and a surface of the lower cover member 102b which faces the inside of the housing 101 will be referred to as an inner surface 102f.

As shown in FIGS. 2A and 2B, the housing 101 has an opening 102c in the corner 100a. Referring to FIG. 2B, for reference, the opening 102c is indicated by the broken line. The opening 102c is arranged between the upper cover member 102a and the lower cover member 102b. The radiation imaging apparatus 100 further includes a buffer member 200 at the corner 100a. The buffer member 200 includes a portion (to be referred to as an inside portion 200a hereinafter) located inside the housing 101 and a portion (to be referred to as an outside portion 200b hereinafter) protruding from the opening 102c of the housing 101 to the outside of the housing 101.

The inside portion 200a of the buffer member 200 is coupled to at least one of the inner surface 102e of the upper cover member 102a and the inner surface 102f of the lower cover member 102b so as not to be removed from the housing 101. The inside portion 200a may be coupled to at least one of the inner surface 102e and the inner surface 102f by, for example, being bonded to it with a bonding agent or adhesive agent. Instead of using this coupling method, the inside portion 200a may be coupled to one of the upper cover member 102a and the lower cover member 102b by being integrally formed with it.

The outside portion 200b of the buffer member 200 includes no portion which is in contact with the outer surfaces 102d and 102g of the outer shell 102. In addition, the outside portion 200b has a step 200c facing a portion of the housing 101 which forms the opening 102c and a space is present between the step 200c and this portion. The step 200c has a shape corresponding to the opening 102c, and is formed in the entire circumference of the outside portion 200b. The step 200c is spaced apart from the opening 102c.

The outer shell 102 is formed from a material having a high elastic modulus (that is, high rigidity), for example, an aluminum alloy, magnesium alloy, fiber-reinforced resin, or fiber-reinforced metal. The upper cover member 102a and the lower cover member 102b may be formed from the same material or different materials. Forming the outer shell 102 using a material having a high elastic modulus in this manner will reduce the deformation of the overall housing 101. This can suppress a situation in which the deformation of the housing 101 causes light to enter the radiation imaging apparatus 100 to result in failure to obtain a good image, or a change in the outer shape of the radiation imaging apparatus 100 makes it impossible to house the apparatus in a gantry or the like.

The buffer member 200 is formed from a material having a lower elastic modulus than the outer shell 102, for example, a resin. The outside portion 200b of the buffer member 200 protrudes from the housing 101 at the corner 100a of the housing 101. For this reason, when the radiation imaging apparatus 100 is dropped, the protruding buffer member 200 collides first with a floor or the like. This can suppress an impact on the outer shell 102. In addition, since the buffer member 200 is coupled to the inner surfaces 102e and 102f of the outer shell 102, the influence of an impact exerted on the outer shell 102 through the buffer member 200 is reduced.

If, for example, the outer shell 102 is formed from a sheet-like fiber-reinforced resin using a long fiber such as prepreg, corners are sometimes molded with cut portions being formed in the material to form it into a nearly rectangular shape. Such cut portions can become breakage starting points. The arrangement of this embodiment can, however, suppress impacts from being applied to the cut portions.

When the outer shell 102 is formed from a fiber-reinforced resin, the buffer member 200 may be formed from a resin which easily allows integral molding with the outer shell 102. When, for example, the outer shell 102 is formed from a carbon-fiber-reinforced resin using epoxy, the buffer member 200 may be formed from a resin compatible with epoxy or a resin containing a short carbon fiber. Forming the outer shell 102 and the buffer member 200 in this manner can form them into a so-called integrally molded product having higher interface strength than when they are bonded to each other. When the outer shell 102 is formed from a metal alloy, the buffer member 200 may be formed from a resin or another material. In addition, in order to increase the bonding strength between the metal and the resin, a mechanical or chemical surface treatment may be applied to each coupling surface.

The radiation imaging apparatus 100 may have the buffer members 200 at all the four corners 100a or at some corners 100a. When the radiation imaging apparatus 100 has the buffer members 200 at some corners 100a, the impact resistance at the corners 100a increases.

Figure 3A:
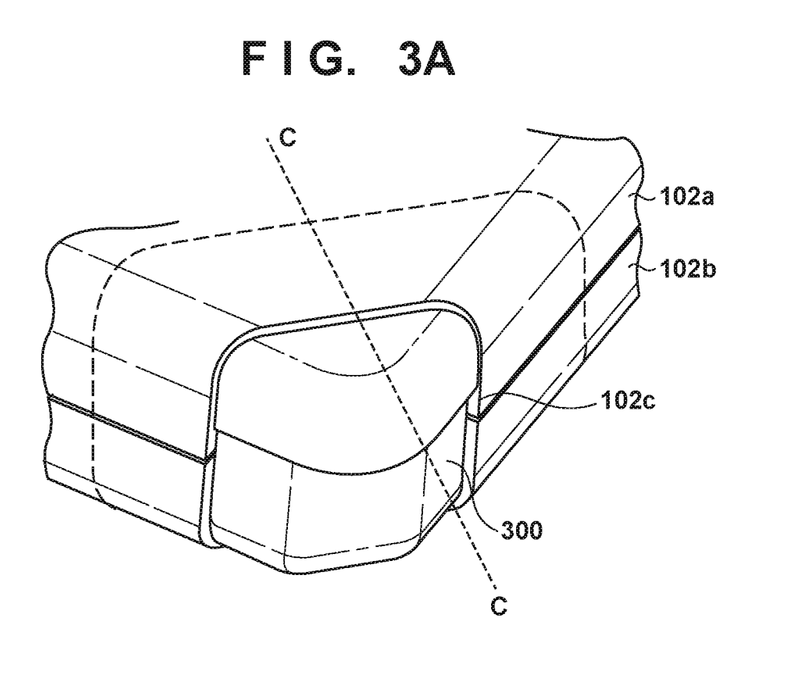
FIGS. 3A and 3B are views for explaining a buffer member according to some other embodiments of the present invention.
Figure 3B:
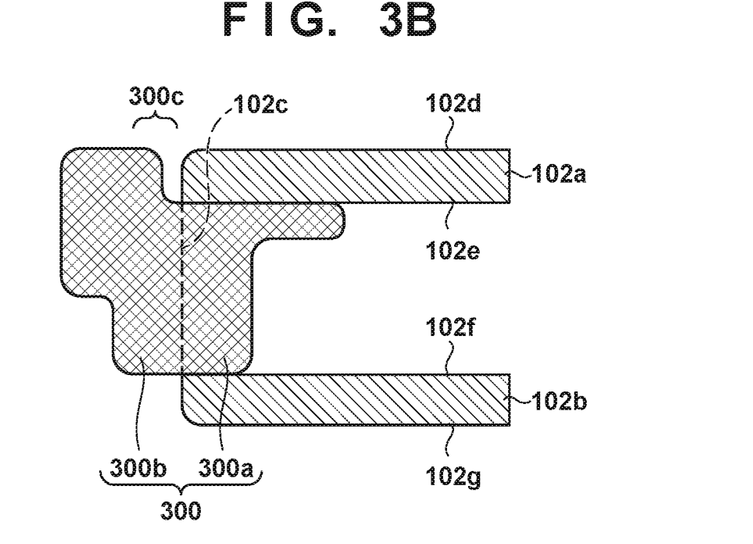

A modification of the radiation imaging apparatus 100 will be described with reference to FIGS. 3A and 3B. FIG. 3A is a perspective view of the corner 100a of the radiation imaging apparatus 100. FIG. 3B is a sectional view taken along a line C-C in FIG. 3A. This modification has a buffer member 300 instead of the buffer member 200. Since other points are the same as those described above, a repetitive description will be omitted. The buffer member 300 differs in shape from the buffer member 200, and other points such as a material and a coupling method for the outer shell 102 may be the same as those concerning the buffer member 200. The buffer member 300 also includes an inside portion 300a inside the housing 101 and an outside portion 300b protruding from the opening 102c of the housing 101 to the outside of the housing 101.

The outside portion 300b of the buffer member 300 includes no portion in contact with the outer surfaces 102d and 102g of the outer shell 102. In addition, the outside portion 300b has a step 300c facing a portion of the housing 101 which forms the opening 102c at an interval. The step 300c has a shape corresponding to a portion of the opening 102c which is located on the incident plane side, and is formed on the incident plane side of the outside portion 300b. The step 300c is spaced apart from the opening 102c.

The outside portion 300b of the buffer member 300 extends farther from the housing 101 on the incident plane side than on the reverse surface side of the housing 101. In addition, the inside portion 300a of the buffer member 300 extends more to the inside of the housing 101 on the incident plane side than on the reverse surface side of the housing 101. When the radiation imaging apparatus 100 is dropped, the portion of the outside portion 300b which extends far from the housing 101 is likely to collide first with a floor or the like. When this extending portion collides first with the floor, a large force is applied to the coupling portion between the buffer member 300 and the upper cover member 102a. Therefore, increasing the area of this coupling portion can reduce the possibility that the buffer member 300 will come off the housing 101.

Another modification of the radiation imaging apparatus 100 may be configured such that the buffer member 300 is inverted. That is, the outside portion 300b of the buffer member 300 may extend farther from the housing 101 on the reverse surface side than on the incident plane side of the housing 101, and the inside portion 300a of the buffer member 300 may extend more to the inside of the housing 101 on the reverse surface side than on the incident plane side of the housing 101.

Figure 4A:
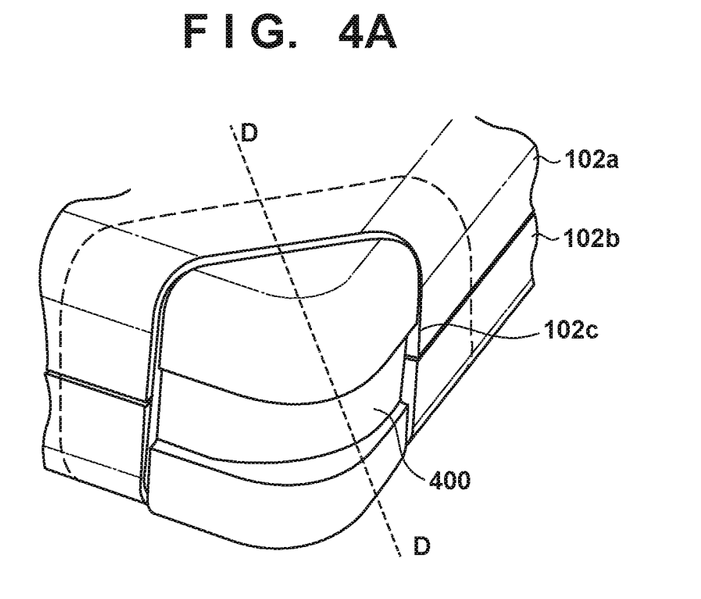
FIGS. 4A and 4B are views for explaining a buffer member according to some other embodiments of the present invention.
Figure 4B:
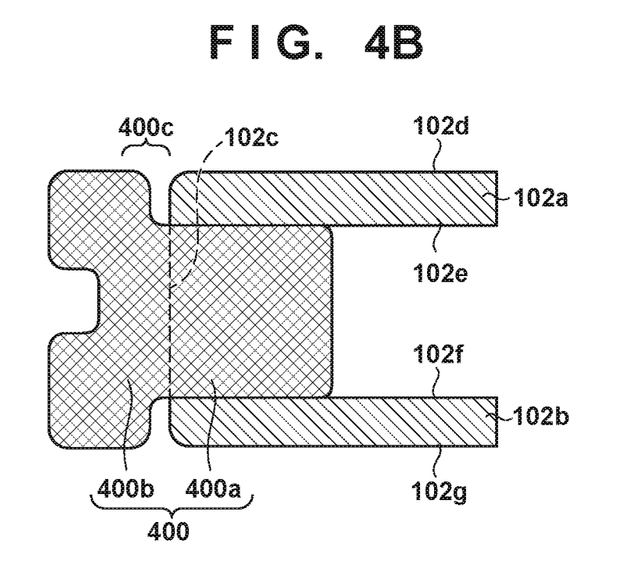

A modification of the radiation imaging apparatus 100 will be described with reference to FIGS. 4A and 4B. FIG. 4A is perspective view of the corner 100a of the radiation imaging apparatus 100. FIG. 4B is a sectional view taken along a line D-D in FIG. 4A. This modification includes a buffer member 400 in place of the buffer member 200. Since other points are the same as those described above, a repetitive description will be omitted. The buffer member 400 differs in shape from the buffer member 200, and other points such as a material and a coupling method for the outer shell 102 may be the same as those concerning the buffer member 200. The buffer member 400 also includes an inside portion 400a inside the housing 101 and an outside portion 400b protruding from the opening 102c of the housing 101 to the outside of the housing 101.

The outside portion 400b of the buffer member 400 includes no portion which is in contact with the outer surfaces 102d and 102g of the outer shell 102. In addition, the outside portion 400b has a step 400c facing a portion of the housing 101 which forms the opening 102c at an interval. The step 400c has a shape corresponding to portions of the opening 102c which are located on the incident plane side and the reverse surface side, and is formed on the incident plane side and reverse surface side of the outside portion 400b. The step 400c is spaced apart from the opening 102c.

The outside portion 400b of the buffer member 400 has a concave portion between a portion on the incident plane side and a portion on the reverse surface side. This can reduce the weight of the buffer member 400 and make a bending moment that expands the housing 101 difficult to be applied to the housing 101.

Figure 5A:
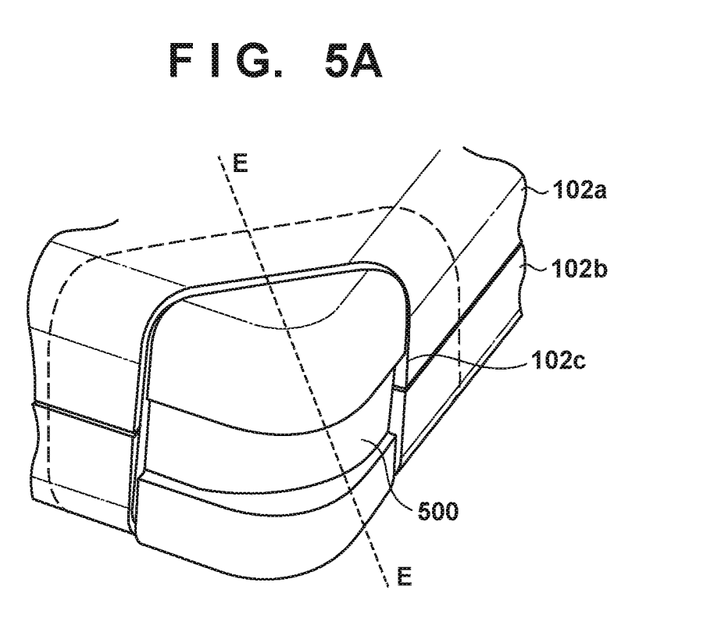
FIGS. 5A and 5B are views for explaining a buffer member according to some other embodiments of the present invention.
Figure 5B:
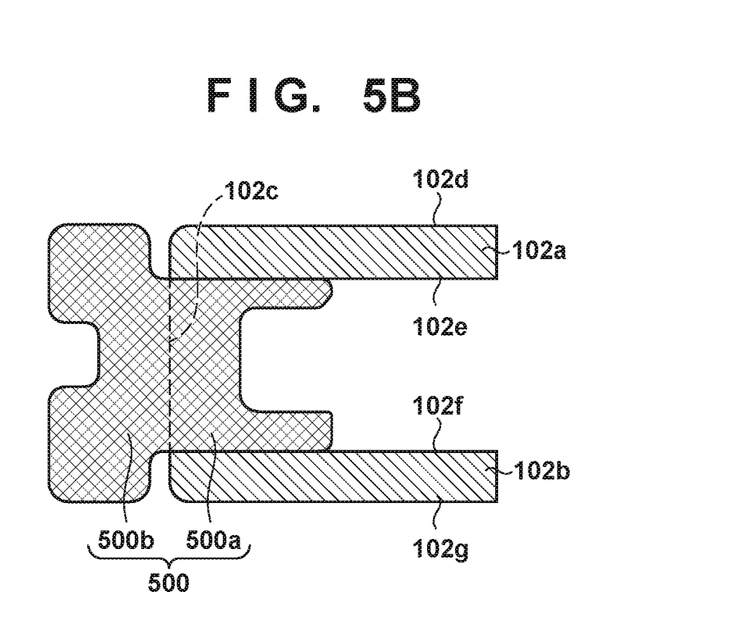

A modification of the radiation imaging apparatus 100 will be described with reference to FIGS. 5A and 5B. FIG.

5A is perspective view of the corner 100a of the radiation imaging apparatus 100. FIG. 5B is a sectional view taken along a line E-E in FIG. 5A. This modification includes a buffer member 500 in place of the buffer member 200. Since other points are the same as those described above, a repetitive description will be omitted. The buffer member 500 differs in shape from the buffer member 200, and other points such as a material and a coupling method for the outer shell 102 may be the same as those concerning the buffer member 200. The buffer member 500 also includes an inside portion 500a inside the housing 101 and an outside portion 500b protruding from the opening 102c of the housing 101 to the outside of the housing 101.

The outside portion 500b of the buffer member 500 has the same shape as that of the outside portion 400b of the buffer member 400. In place of this shape, the outside portion 500b of the buffer member 500 may have the same shape as that of the outside portion of another buffer member described above. The inside portion 500a of the buffer member 500 has a concave portion in a surface which is not in contact with the housing 101 (that is, a surface facing the inside of the housing 101). This can reduce the weight of the buffer member 500 while maintaining the coupling force between the buffer member 500 and the housing 101.

Figure 6A:
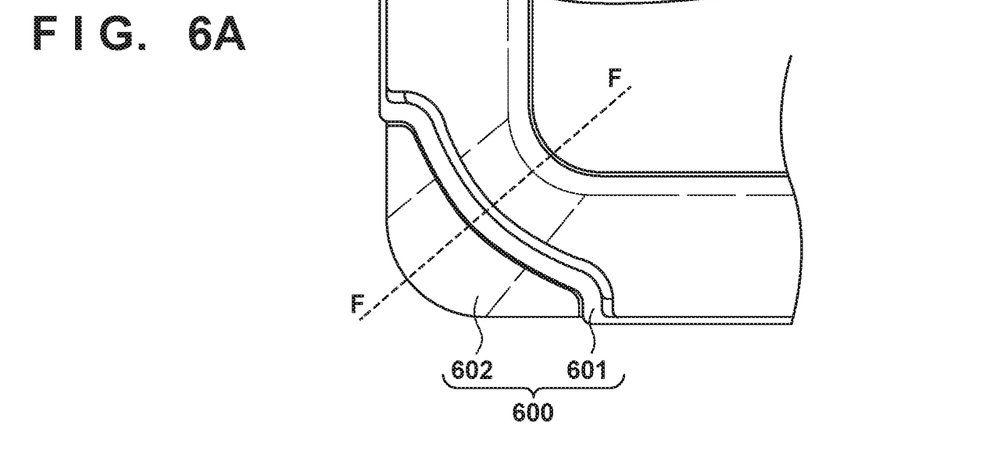
FIGS. 6A to 6C are views for explaining a buffer member according to some other embodiments of the present invention.
Figure 6B:
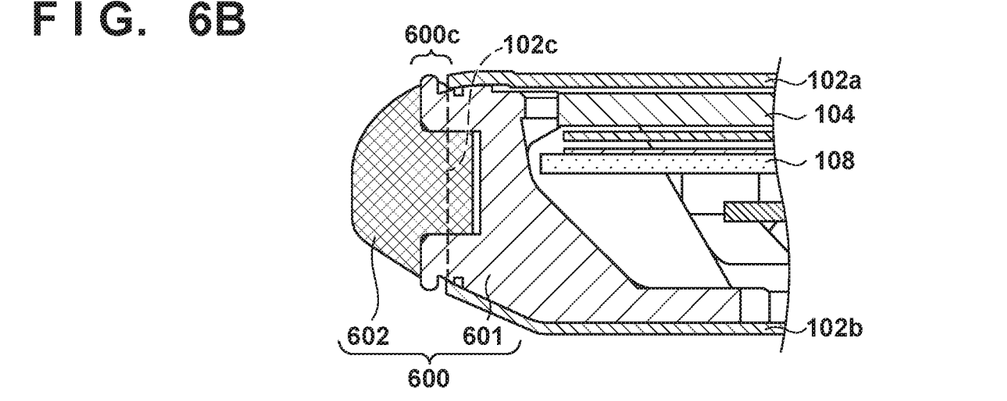
Figure 6C:
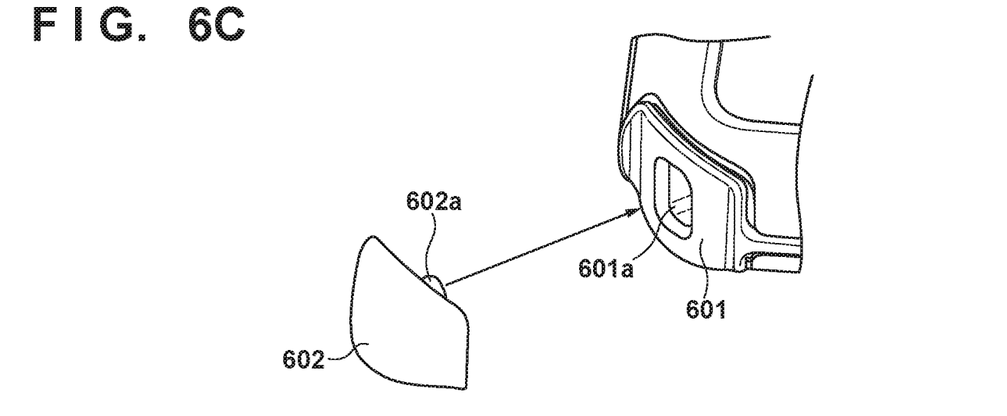

A modification of the radiation imaging apparatus 100 will be described with reference to FIGS. 6A to 6C. FIG. 6A is a plan view of the radiation imaging apparatus 100 with a focus being placed on the corner 100a. FIG. 6B is a sectional view taken along a line F-F in FIG. 6A. FIG. 6C shows a state in which a second member 602 is removed from a first member 601. This modification includes a buffer member 600 in placed of the buffer member 200. The buffer member 600 includes an inside portion inside the housing 101 and an outside portion protruding from the opening 102c of the housing 101 to the outside of the housing 101.

The outside portion of the buffer member 600 includes no portion which is in contact with the outer surfaces 102d and 102g of the outer shell 102. In addition, the outside portion of the buffer member 600 has a step 600c facing a portion of the housing 101 which forms the opening 102c at an interval. The step 600c has a shape corresponding to the opening 102c, and is formed in the entire circumference of the outside portion 600b. The step 600c is spaced apart from the opening 102c.

The buffer member 600 is constituted by the first member 601 and the second member 602. The first member 601 is formed from the same material as that of the buffer member 200, and is coupled, like the buffer member 200, to at least one of the inner surface 102e of the upper cover member 102a and the inner surface 102f of the lower cover member 102b so as not to be removed from the housing 101. The outside portion of the buffer member 600 is constituted by part of the first member 601 and part of the second member 602. The second member 602 is formed from a material having a lower elastic modulus than the first member 601, for example, a foam or gel material. The second member 602 has a convex portion 602a having a shape corresponding to a concave portion 601a of the first member 601. Inserting the convex portion 602a into the concave portion 601a will attach the second member 602 to the first member 601. The second member 602 may be bonded to the first member 601 with a bonding agent or adhesive agent or mechanically. When the radiation imaging apparatus 100 is dropped, the second member 602 of the buffer member 600 collides first with a floor or the like. Since the second member 602 has a lower elastic modulus than the first member 601, the buffering ability of the buffer member 600 increases more.

Figure 7A:
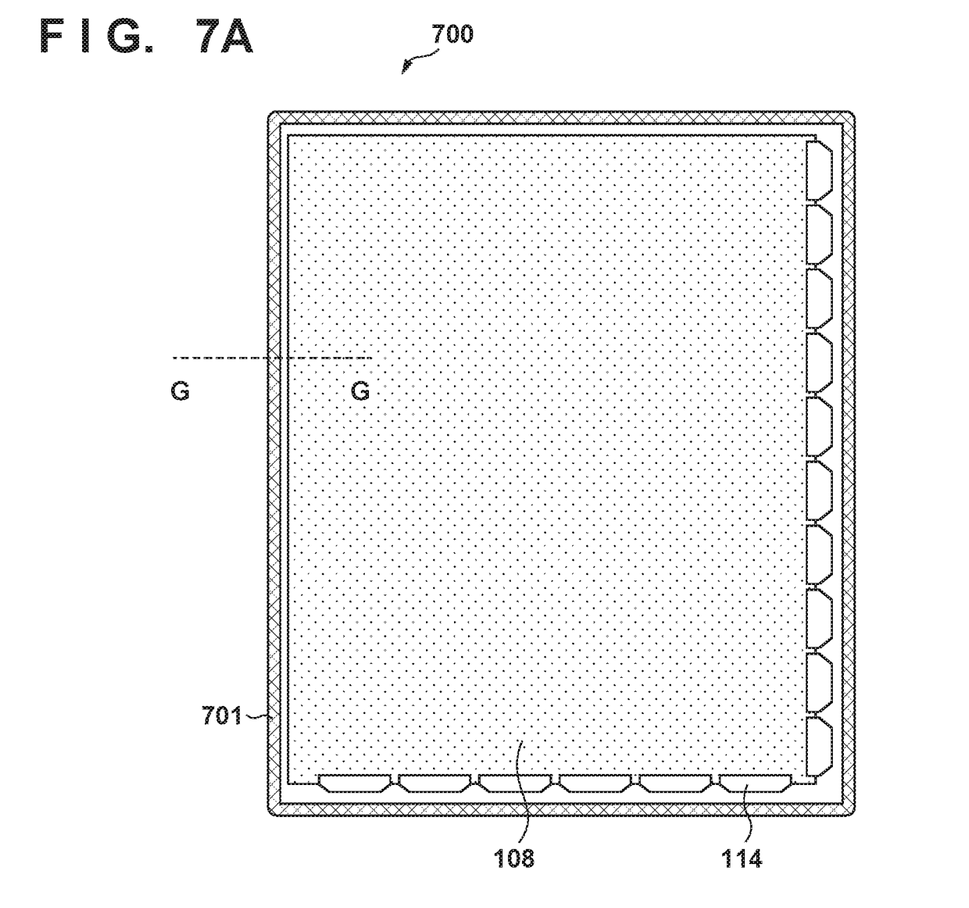
FIGS. 7A and 7B are views for explaining a radiation imaging apparatus according to some other embodiments of the present invention.
Figure 7B:
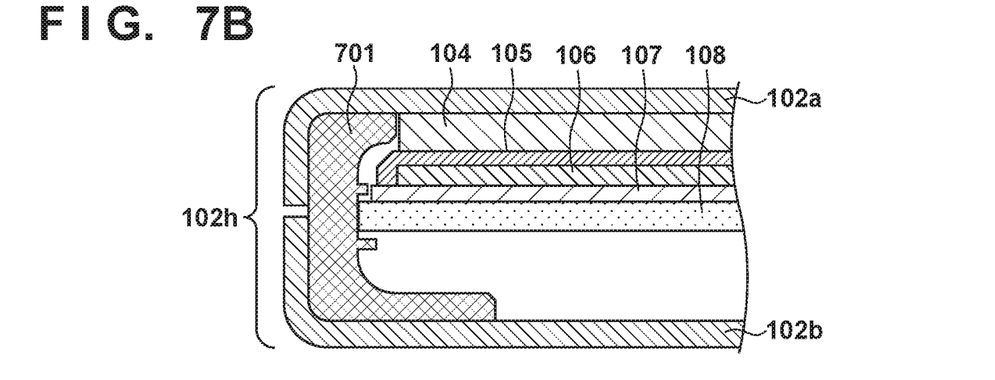

The arrangement of a radiation imaging apparatus 700 according to some embodiments of the present invention will be described with reference to FIGS. 7A and 7B. FIG. 7A is a plan view of the radiation imaging apparatus 700. FIG. 7B is a sectional view taken along a line G-G in FIG. 7A. The radiation imaging apparatus 700 may be the same as the radiation imaging apparatus 100 except that it includes a buffer member 701 instead of the buffer member 200. The buffer member 701 differs in shape from the buffer member 200, and other points such as a material and a coupling method for the outer shell 102 may be the same as those concerning the buffer member 200. The buffer member 701 also includes an inside portion inside the housing 101 and an outside portion protruding from the opening 102c of the housing 101 to the outside of the housing 101. The shape of the outside portion of the buffer member 701 may be the same as that of any of the buffer members described above.

The buffer member 701 has a frame shape surrounding the detection panel constituted by the sensor board 107 and the scintillator layer 106. The buffer member 701 may be an integral member or may be formed by coupling a plurality of members to each other. In addition, the buffer member 701 may have a cut portion in part of the frame shape. The inside portion of the buffer member 701 extends along a side wall 102h of the outer shell 102 (that is, a side wall of the housing 101). The buffer member 701 is positioned by the outer shell 102, and hence may or may not be coupled to the outer shell 102. Having the frame shape, the buffer member 701 can not only suppress as much as possible the deformation of the radiation imaging apparatus 700 caused by a dropping impact but also improve the bending rigidity of the overall radiation imaging apparatus 700.

As shown in FIG. 7B, the base 108 may be in contact with the buffer member 701. This can downsize the radiation imaging apparatus 700. In addition, the buffer member 701 may have a concave portion in a surface which is not in contact with the housing 101 (that is, a surface facing the inside of the housing 101). This concave portion may be arranged in the entire circumference of the buffer member 701 having the frame shape. The edge of the base 108 may be fitted in the concave portion of the buffer member 701.

The buffer member 701 may partially include a conductor such as a metal or may be formed from a material having conductivity such as a fiber-reinforced resin. Arranging a frame-shaped conductive member surrounding the radiation detection panel can reduce noise coming from the outside of the radiation imaging apparatus 700 to the radiation detection panel.

Figure 8:
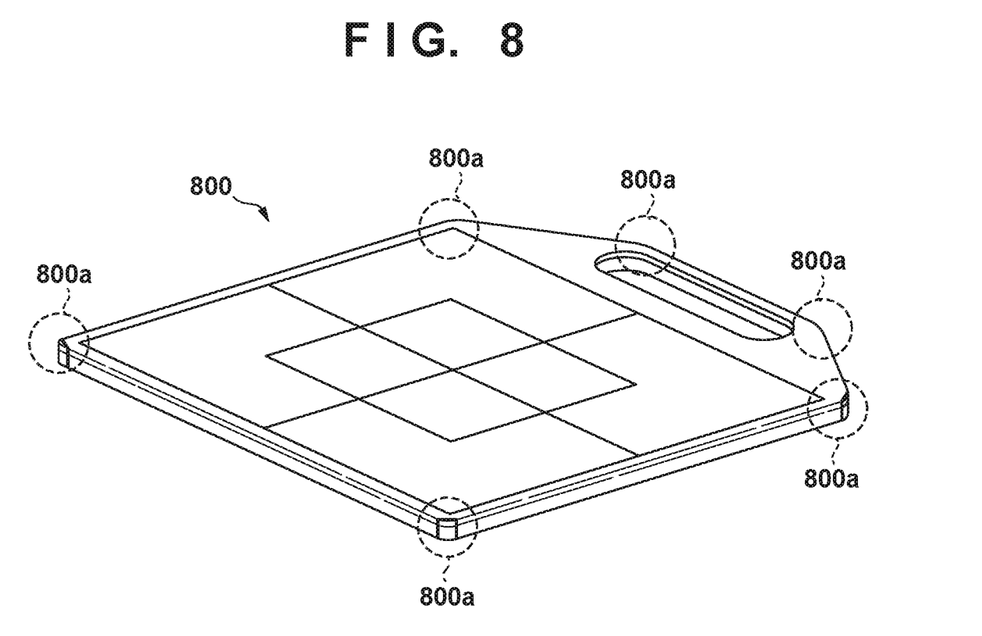
FIG. 8 is a view for explaining a radiation imaging apparatus according to some other embodiments of the present invention.

The arrangement of a radiation imaging apparatus 800 according to some embodiments of the present invention will be described with reference to FIG. 8. The housing of the radiation imaging apparatus 800 has a hexagonal shape and a grip portion. The radiation imaging apparatus 800 includes any of the buffering members described above. The buffering member has a portion protruding from an opening in at least one of corner portions 800a of the radiation imaging apparatus 800.

Figure 9:
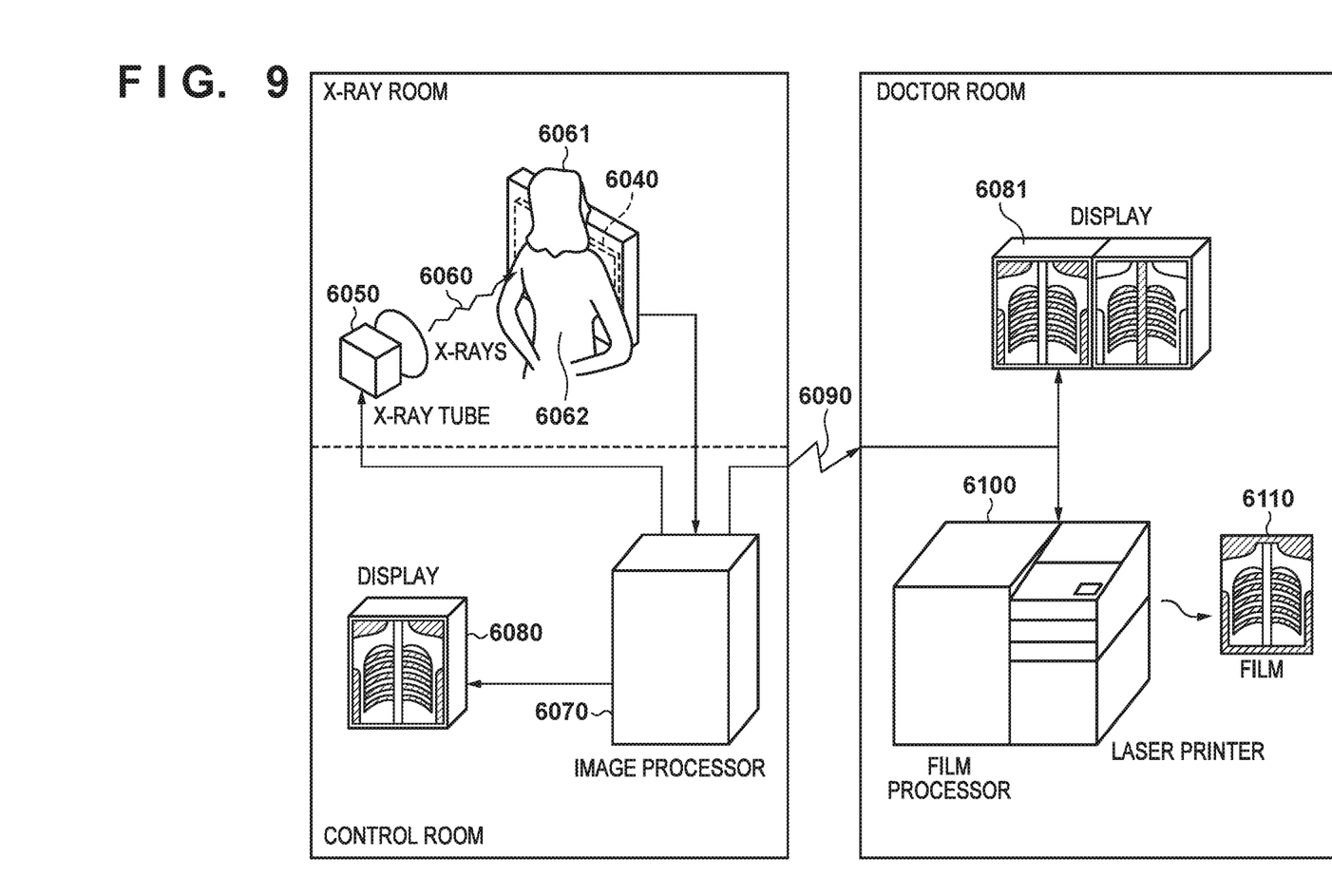
FIG. 9 is a view for explaining a radiation imaging system according to some embodiments of the present invention.

FIG. 9 is a view showing an application example of the radiation imaging apparatus according to the present invention to an X-ray diagnostic system (radiation imaging system). X-rays 6060 generated as radiation by an X-ray tube 6050 (radiation source) are transmitted through a chest region 6062 of an object or a patient 6061 and enter a detection apparatus 6040 as one of the above radiation imaging apparatuses. The incident X-rays include information about the inside of the body of the patient 6061. The scintillator emits light as X-rays enter, and electrical information is obtained by photoelectric conversion. This information is converted into a digital signal. An image processor 6070 serving as a signal processing unit performs image processing of the signal. It is possible to observe the resultant image on a display 6080 serving as a display unit in a control room. Note that the radiation imaging system includes at least a detection apparatus and a signal processing unit which processes signals from the detection apparatus.

In addition, it is possible to transfer this information to a remote place via a transmission processing unit such as a telephone line 6090. The information can be displayed on a display 6081 as a display unit in another place such as a doctor room or can be stored in a recording unit such as an optical disk. This makes it possible for a doctor in a remote place to perform diagnosis. In addition, a film processor 6100 as a recording unit can record the information on a film 6110 as a recording medium.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiation imaging apparatus comprising:
a radiation detection panel;
a housing having a square shape configured to accommodate the radiation detection panel; and
four corner members respectively disposed separately at each corner of the housing for effectively dealing with impact, wherein
material of the corner members is different from that of the housing.

2. The apparatus according to claim 1, wherein the material of the housing is a fiber-reinforced resin.

3. The apparatus according to claim 1, wherein all of the corner members have the same material.

4. The apparatus according to claim 1, wherein all of the corner members have the same shape.

5. The apparatus according to claim 1, wherein the material of the corner members is a resin.

6. The apparatus according to claim 1, wherein the housing provides an incident plane that is irradiated with radiation, a reversed surface opposite to the incident plane and a side surface connecting the incident plane and the reversed surface,
an opening is formed at the side surface in each of the corners, and
at least one of the corner members includes a first portion fixed inside the housing and a second portion protruding from the opening of the housing to an outside of the housing.

7. The apparatus according to claim 6, wherein the first portion of the corner member is bonded to an inner surface of the housing.

8. The apparatus according to claim 6, wherein the first portion of the corner member is integrally molded on the housing.

9. The apparatus according to claim 6, wherein the first portion of the corner member has a frame shape surrounding the radiation detection panel.

10. The apparatus according to claim 6, wherein the first portion of the corner member extends along the side surface of the housing.

11. The apparatus according to claim 6, wherein the first portion of the corner member has a concave portion in a surface which is not contact with the housing.

12. The apparatus according to claim 6, wherein the second portion of the corner member has a step facing a portion, of the housing, which forms the opening and a space is present between the step and the portion.

13. The apparatus according to claim 12, wherein the step has a shape corresponding to at least part of the opening.

14. The apparatus according to claim 6, further comprising a base configured to support the radiation detection panel, wherein
the base is in contact with the corner member.

15. The apparatus according to claim 6, wherein an elastic modulus of the second portion of the corner member is lower than that of a portion of the housing which forms the opening.

16. The apparatus according to claim 1, wherein the housing provides openings at each corner of the square shape such that each corner of the housing is cut-off, and
the corner members are disposed at each opening to compensate for the cut-off portions of the housing.

17. The apparatus according to claim 6, wherein the first portion of the corner member faces an internal space of the housing where the radiation detection panel is located.

18. The apparatus according to claim 6, wherein the opening penetrates the housing.

19. A radiation imaging system comprising:
the radiation imaging apparatus according to claim 1; and
a processing apparatus for processing a signal obtained by the radiation imaging apparatus.

20. A radiation imaging apparatus comprising:
a radiation detection panel;
a housing having a rectangular shape configured to accommodate the radiation detection panel; and
four corner members respectively disposed separately at each corner of the housing for effectively dealing with impact, wherein material of the corner members is different from that of the housing.

* * * * *